(12) United States Patent
Khanuja et al.

(10) Patent No.: US 6,767,876 B2
(45) Date of Patent: Jul. 27, 2004

(54) **COMPOSITION AND PROCESS FOR PREPARING DISINFECTANTS COMPRISING *MENTHA SPICATA* VAR. VIRIDIS AND THEIR USE**

(75) Inventors: Suman Preet Singh Khanuja, Uttar Pradesh (IN); Mahendra Pandurang Darokar, Uttar Pradesh (IN); Tirupadiripuliyur Ranganathan Santhakumar, Uttar Pradesh (IN); Ajit Kumar Shasany, Uttar Pradesh (IN); Krishna Kumar Aggrawal, Uttar Pradesh (IN); Atique Ahmed, Uttar Pradesh (IN); Pushplata Chaturvedi, Uttar Pradesh (IN); Vivek Kumar Gupta, Uttar Pradesh (IN); Alok Krishna, Uttar Pradesh (IN); Anil Kumar Singh, Uttar Pradesh (IN); Janak Raj Bahl, Uttar Pradesh (IN); Ravi Prakash Bansal, Uttar Pradesh (IN); Dinesh Kumar, Uttar Pradesh (IN)

(73) Assignees: Council of Scientific and Industrial Research, New Delhi (IN); Department of Biotechnology, New Delhi (IN)

( * ) Notice: Subject to any disclaimer, the term of this patent is extended or adjusted under 35 U.S.C. 154(b) by 0 days.

(21) Appl. No.: 10/385,154

(22) Filed: Mar. 10, 2003

(65) Prior Publication Data
US 2004/0014620 A1 Jan. 22, 2004

(30) Foreign Application Priority Data
Mar. 28, 2002 (ID) .................................... P00200200158

(51) Int. Cl.$^7$ ................................................ A61K 7/50
(52) U.S. Cl. ...................... 510/137; 510/138; 510/159; 510/420; 510/463; 510/499
(58) Field of Search ................................ 510/137, 138, 510/159, 420, 463, 499

(56) References Cited

PUBLICATIONS

Harvey Wickes Felter, M.D. et al, "oleum Mentae Viridis (U.S. P.)–Oil of Spearint", King's American Dispensatory, 1898 *nma.*

* cited by examiner

*Primary Examiner*—Necholus Ogden
(74) *Attorney, Agent, or Firm*—Merchant & Gould P.C.

(57) ABSTRACT

The present invention relates to disinfectant and cleansing compositions for cleaning the skin of humans and for cleaning surface such as floors, and the invention also provides process for the preparation of the said composition.

17 Claims, No Drawings

US 6,767,876 B2

COMPOSITION AND PROCESS FOR PREPARING DISINFECTANTS COMPRISING *MENTHA SPICATA* VAR. VIRIDIS AND THEIR USE

TECHNICAL FIELD

The present invention relates to disinfectant compositions for cleaning the skin of humans and for cleaning surface such as floors. The compositions are homogeneous, clear, and also useful as disinfectant. The invention also provides a process for the preparation of the cleaning composition. The composition of the invention includes essential oils isolated from plants. The compositions are prepared by mixing the components in a particular well-defined order to obtain clear, transparent solutions effective against pathogenic bacteria and fungi.

BACKGROUND ART

The invention relates to development of the disinfectants that are non-toxic, bio-safe and in addition give pleasant odour. The disinfectants already available in the market contain harmful chemicals such as formaldehyde, ethane dialdehyde, n-propanol, benzalkonium chloride, phenol and the like.

Essential oils isolated from plant sources are known to possess antimicrobial properties. However when used as disinfectants in hospitals, laboratories, offices and houses, they run into problems, such as—not dispersing evenly in common solutions like water. Thus, a composition circumventing these bottlenecks is most desirable and is the intent of the invention.

OBJECTS OF THE INVENTION

Accordingly, the main object of the invention is to provide a disinfectant compositions for cleaning skin.

Another object is to provide a surface cleaning composition.

Yet another object is to provide a process for the preparation of the surface cleaning composition.

Still another object is to provide a process for the preparation of the skin cleaning composition.

SUMMARY OF THE INVENTION

The invention relates to the process for preparing homogeneous, clear, disinfectant compositions, such as for example, hand and surface cleaning compositions that contain essential oils isolated from plants. The compositions are prepared by mixing the components in a particular well-defined order on the basis of experimentation to obtain clear, transparent solutions effective against pathogenic bacteria and fungi. The process of the invention includes the defined sequence of steps of mixing together all the constituents intimately as described in the examples.

DETAILED DESCRIPTION OF INVENTION

The invention provides a process for preparing the highly effective hand and surface disinfectants, which kill a broad spectrum of the disease causing germs and also removes dirt and stains completely with ease by using various plant essential oils. The disinfectants are able to kill all the pathogenic bacterial and fungal strains tested at the recommended concentration. They are non-corrosive and bio-safe.

The hand disinfectant composition is effective for instant hand wash/cleaning. The use requires pouring out a few drops and rubbing well over hands and palm for 30 sec. It can be used in the laboratories of microbiology to cell culture and for hospitals. It gives a healthy environment to all researchers and professionals and also a bio-safe hand wash for household and toiletries.

The surface disinfectant can be used on surfaces like kitchen platform, cabinets, floors, ceramic tiles, bathrooms etc. These highly effective surface disinfectant compositions are useful for ware washing and cleaning hard surfaces, rinsing, sanitizing, and the like. As such, the invention provides a homogeneous, clear and transparent solution for cleaning hands and other human skin surfaces, said composition comprising:

| | |
|---|---|
| a. oil obtained from the plant *Mentha spicata* var. viridis: | 0.01–0.05% |
| b. Menthol Menthyl acetate (MMA): | 0.05–0.5% |
| c. Ethanol: | 1–25% |
| d. Isopropanol: | 5–50% |
| e. Benzalkonium Chloride: | 0.1–0.5%, and |
| f. Distilled water: | to make up the volume. |

The above composition is termed as "HK" and is referred as such in the application.

The above composition "HK" preferably comprises:

| | |
|---|---|
| a. *Mentha spicata* var. viridis oil: | 0.02% |
| b. Menthol Menthyl acetate: | 0.10% |
| c. Ethanol: | 5.00% |
| d. Isopropanol: | 30.00% |
| e. Benzalkonium Chloride: | 0.30%, and |
| f. Distilled water: | to make up the volume. |

The Applicant has found that the above ingredients when mixed together form a synergistic composition and surprisingly are found to exhibit disinfectant and cleansing properties. The Applicant also found that if the ingredients are mixed in any other order or in any other proportion, the desired effects are not exhibited. The composition has been arrived at after much experimentation and trial.

In addition, the invention provides a homogeneous, clear and transparent solution for cleaning surfaces, said composition comprising:

| | |
|---|---|
| a. *Mentha spicata* var. viridis oil: | 0.01–0.05% |
| b. Citronella oil: | 0.005–0.05% |
| c. 2-ethoxyethanol: | 0.05–1.0% |
| d. Benzalkonium chloride: | 0.05–5.0% |
| e. Sodium hydroxide: | 0.0001–0.2 N, and |
| f. Sodium lauryl sulphate: | 0.001–1.0% |

This composition is termed as "SW" and is referred as such in the application. This composition preferably comprises:

| | |
|---|---|
| a. *Mentha spicata* var. viridis oil: | 0.02%; |
| b. Citronella oil: | 0.01% |
| c. 2-ethoxyethanol: | 0.1% |
| d. Benzalkonium chloride: | 0.1% |
| e. Sodium hydroxide: | 0.0005 N, and |
| f. Sodium lauryl sulphate: | 0.0025% |

The Applicant has found that the above ingredients when mixed together form a synergistic composition and surprisingly are found to exhibit disinfectant and cleansing properties. The Applicant also found that if the ingredients are mixed in any other order or in any other proportion, the desired effects are not exhibited.

As used above, *Mentha spicata* L. var. viridis is a naturally growing plant found on the shores of the River Ganga in India. This mint plant is a distinctive variety capable of being propagated vegetatively by suckers. The plant exhibits unique and profuse canopy and height surpassing all existing mint varieties. The most interesting aspect of this plant is that the essential oil extracted from the plant grown for 45 days or more exhibits anti-insect and anti-microbial properties. The essential oil yielded by the plant is in the range of 0.4–0.6%, which is far greater than the existing varieties. The oil comprises a combination of:
(i) 1.50 to 6.52% limonene,
(ii) 0.107 to 4.42% carvone and
(iii) 28.50 to 80.45% piperitenone.

The said plant *Mentha spicata* L. var. viridis is the subject of U.S. patent application Ser. No. 09/633,066. The seeds of this plant can be freely obtained from the Central Institute of Medicinal and Aromatic Plants, Lucknow, India. This is a Government-funded organisation and the seeds of this plant are distributed for research and commercial purposes without any fee. The oil of the plant is also readily available with the Institute and few other places.

Further, the invention provides a process for the preparation of a hand and surface cleaning and disinfectant composition termed "HK", which composition is effective against pathogenic bacteria and fungi, said process comprising the steps of:
a. providing *Mentha spicata* var. viridis oil to the extent of 0.01 to 0.05%,
b. adding a 0.05 to 0.5% combination of menthol and menthyl acetate to the oil of step (a) and mixing thoroughly,
c. adding 5 to 25% ethanol to the mix of step (b) and mixing thoroughly,
d. adding 5 to 50% isopropyl alcohol to the mix of step (c) and mixing the entire combination thoroughly,
e. adding distilled water to the mix of step (d) and mixing the entire combination thoroughly, and
f. adding 0.1 to 0.5% benzalkonium chloride to the mix of step (e) and mixing the entire combination thoroughly to obtain a disinfectant composition.

In an embodiment, the oil of *Mentha spicata* var. viridis is obtained from the leaves of the plant by hydro-distillation using Clevenger apparatus.

In another embodiment, the combination of menthol and menthyl acetate is prepared by mixing menthol and menthyl acetate in the ratio of 40:60(w/v).

In still another embodiment, menthol is obtained crystallization at minus 60° C. of oil isolated from the plant *Mentha arvensis*.

In yet another embodiment, menthol is obtained by direct or azeotropic esterification of menthol with acetic acid.

In an embodiment, the composition "HK" is used by pouring out a few drops and rubbing well over the hands for 30 sec.

In another embodiment, the process for the preparation of a surface cleaning and disinfectant composition termed "SW" comprises the steps of:
a. providing *Mentha spicata* var. viridis oil to the extent of 0.01 to 0.05%,
b. adding 0.005 to 0.5% citronellol oil to the oil of step (a) and mixing both throughly,
c. adding 0.05 to 1% of 2-ethoxyethanol to the mix of step (b) and mixing the ingredients thoroughly,
d. adding 0.05 to 5% benzalkonium chloride to the mix of step (c) and mixing the entire combination thoroughly
e. adding 0.0001 to 0.2N% sodium hydroxide to the mix of step (d) and mixing the entire combination thoroughly,
f. adding 0.001 to 1% sodium lauryl sulphate to the mix of step (e) and mixing the entire combination thoroughly, and
g. distilled water to the mix of step (f) and mixing the entire combination thoroughly to obtain a surface cleaning and disinfectant composition.

In an embodiment, the oil of *Mentha spicata* var. viridis is obtained from the leaves of the plant by hydro-distillation using Clevenger apparatus.

In another embodiment, citronella oil is obtained from the leaves of plant commonly called 'Citronella' or *Cymbopogon winterianus*.

In still another embodiment, the oil from the plant *Cymbopogon winterianus* is obtained by hydro-distillation.

In yet another embodiment, the surface disinfectant composition "SW" is applied onto a piece of soft wet cloth and the same is spread over the infected area and left for 5 minutes for effective disinfection. In another embodiment, the composition "SW" is used to effectively clean decontaminate the surfaces are kitchen platform, ceramic tiles, marbles, cabinets, tables, and likewise. The composition is used in the range of 1X to 100X.

The following experiments shown as examples of the invention were critically performed to formulate and use the herbal disinfectants of surfaces and hands and skin possessing anti-microbial action development.

EXAMPLE 1

Preparation of First Level Combination

First level combination (MMA) is prepared by mixing menthol and menthyl acetate in the ratio of 40:60 (W/V). Menthol is obtained by crystallization at minus 60° C. of oil isolated from *Mentha arvensis* commonly referred to as Menthol Mint. Crystallization of L-menthol was carried out by slow and gradual chilling of the oil up to –60° C. in deep freezer (Tandon, et al., *J. Med. Arom. Plant Sci.*, 1998, 20: 25–27). Menthyl acetate occurs naturally in mint oil however the content is very low and hence the isolation procedure may be laborious. Therefore, the menthyl acetate was prepared by direct or azeotropic esterification of menthol with corresponding acid ie., acetic acid and therefore can be produced in large quantities (Arctander, S., In *Perfume and flavor chemicals*. Vol-1, Montclair; N.J., No.1845–1852; Ahmad, A., et al., *J. Essent. Oil Res.*, 2000, 12 In Press). $^1$H and $^{13}$C-NMR, Mass and IR spectra confirmed the structure of the acyl derivative.

EXAMPLE-2

Preparation of '*Mentha spicata* var. Viridis' Oil and 'Citronella' Oil

Essential oil rich in piperitenone oxide of the leaves of *Mentha spicata* var. viridis was isolated by hydro-distillation process using clavenger apparatus. The process of hydro-distillation is known and can be performed by a person skilled in the art. The citronella oil was also obtained by hydro-distillation of the leaves of plant commonly called 'Citronella' (*Cymbopogon winterianus*). Both citronella and Mentha spicata var. viridis oil were stored in the refrigerator until use. The major constituents of these oils were analyzed and identified using standards by Gas-Liquid chromatography (GLC). Both these plant materials are available as planting/seed materials for cultivation at CIMAP (Central Institute of Medicianl and Aromatic Plants, Lucknow, India). In addition citronella oil is also available in the market. The composition of both Mentha spicata var viridis oil and the Cymbopogon winterianus (citronella) oils are provided hereinbelow:

Constituents of Mentha spicata var viridis oil as determined by GLC:

Total oil yield=0.36 to 0.65%; Limonene=1.50 to 6.52%; Carvone=0.10 to 4.42%; Piperitenone oxide=28.5 to 77.48%.

Constituents (%) of Cymbopogon winterianus oil as determined by GLC:

Total oil yield=0.80; Methyl heptenone=0.97; Linalool=0.57; Geraniol=23.3; Elemol=10.67; Geranyl acetate=3.27; bisafalol=1.48; Citronellol=9.92; Limonene=1.50; Citronellal=35.94.

EXAMPLE-3

Preparation of Surface Disinfectant "SW"

The surface disinfectant "SW" is prepared in a step-wise manner as described below:

A) First a solution of sodium hydroxide (0.0005 N) and sodium lauryl sulphate (0.0025%) (referred as solution B) is prepared.

B) To prepare one litre of 100X 'SW', mix all the constituents in the following order:

1. Take 20 ml Mentha spicata var. viridis oil in a 1000 ml measuring cylinder
2. Add 10 ml Citronella oil to it and mix
3. Add 100 ml 2-ethoxyethanol and again mix properly
4. Now make up the volume with solution B.
5. Then add 100 ml benzalkonium chloride C) The final composition of SW will be

| | |
|---|---|
| Mentha spicata var. viridis: | 0.02%; (range 0.01–0.05%) |
| Citronella oil: | 0.01%; (range 0.005–0.05%) |
| 2-ethoxyethanol: | 0.1%; (range 0.05–1.0%) |
| Benzalkonium chloride: | 0.1%; (range 0.05–5.0%) |
| Sodium hydroxide: | 0.0005 N (range 0.0001–0.2 N) and |
| Sodium lauryl sulphate: | 0.0025% (range 0.001–1.0%) |

If the constituents are not mixed in the order given above the resultant solution will not be clear and transparent and hence will not be effective against the bacteria and fungi.

EXAMPLE-4

Preparation of Hand and Skin Disinfectant 'HK'

Based on the antimicrobial activity detected in the oils of many higher plants a hand disinfectant called 'HK' which consist of Herbal essential oils with anti-microbe action, Iso-propanol, Ethanol, Benzalkonium chloride, permitted coloring agents was developed. The composition and method of preparation of 'HK' is mentioned below.

To prepare one litter of 'HK', mix all the constituents in the following order.

1. Take 0.2 ml of Mentha spicata var. viridis oil in a measuring cylinder.
2. Add 1.0 ml of first level combination (MMA) to it and mix.
3. Add 50 ml of ethanol and mix thoroughly.
4. Add 300 ml of isopropyl alcohol and mix gently.
5. Make up the volume to 997 ml with distilled water.
6. Add 3.0 ml of benzalkonium chloride.

If the constituents are not mixed in the order given above the resultant solution will not be clear and transparent and hence will not be effective against the bacteria and fungi.

The resulting solution will have a composition of

| | |
|---|---|
| Mentha spicata var. viridis: | 0.02% (range 0.01–0.05%) |
| MMA: | 0.10% (range 0.05–0.5%) |
| Ethanol: | 5.00% (range 1–25%) |
| Isopropanol: | 30.00% (range 5–50%) |
| Benzalkonium Chloride: | 0.30% (range 0.1–0.5%) |
| Distilled water: | to make up the volume. |

EXAMPLE-5

Evaluation of the Antiseptic Property of the Disinfectants

For assessing the antiseptic properties, the disinfectants were tested against a screen of human pathogenic bacteria and fungi.

The bacteria used are as shown hereblow in Table 1.

TABLE 1

Bacterial and fungal strains used and their growth conditions.

| Sl. no | Name of the micro-organism | Strain designation/ Source[a] | Incubation temperature employed (° C.) | Medium used[b] |
|---|---|---|---|---|
| I. BACTERIAL STRAINS | | | | |
| 1 | Bacillus subtilis (BS) | MTCC 121 | 30 | MH |
| 2 | Enterobacter aerogenes (EA) | MTCC 111 | 30 | MH |
| 3 | Enterococcus faecalis (EF) | MTCC 439 | 37 | MH |
| 4 | Klebsiella pneumoniae (KP) | MTCC 109 | 37 | MH |
| 5 | Pseudomonas aeruginosa (PA) | MTCC 741 | 37 | MH |
| 6 | Staphylococcus aureus (SA) | MTCC 96 | 37 | MH |
| 7 | Streptococcus mutans (SM) | MTCC 890 | 37 | BHI |
| 8 | Yersinia enterocolitica (YE) | MTCC 861 | 30 | MH |
| 9 | Salmonella typhi (SY) | MTCC 733 | 37 | MH |
| 10 | Escherichia coli (EC) | MTCC 723 | 37 | MH |
| 11 | Staphylococcus epidermidis (SE) | MTCC 435 | 37 | MH |
| 12 | Mycobacterium smegmatis (MS) | UDSC | 37 | MH |
| II. FUNGAL STRAINS | | | | |
| 13 | Microsporum gypseum (MG) | AIIMS | 28 | SDA |
| 14 | Aspergillus niger (AN) | AIIMS | 28 | SDA |
| 15 | Aspergillus flavus (AF) | AIIMS | 28 | SDA |
| 16 | Trichophyton rubrum (TR) | AIIMS | 28 | SDA |
| 17 | Sporothrix schenckii (SS) | AIIMS | 28 | SDA |
| 18 | Candida albicans Al (CI) | AIIMS | 28 | SDA |
| 19 | Candida albicans (CA) | MTCC | 28 | SDA |
| 20 | Histoplasma capsulatum (HC) | PGI | 28 | SDA |
| 21 | Cryptocoous neoformans (CN) | PGI | 28 | SDA |

[a]MTCC, Microbial type culture collection; UDSC, University of Delhi South Campus; AIIMS, All India Institute of Medical Sciences, PGI, Post-Graduate Medical Education & Reasearch Institute.
[b]MH, Mueller-Hinton agar; BHI, Brain heart infusion agar; SDA, Sabauraud dextrose agar.

The disinfectants were used as such or diluted in dimethyl sulfoxide to the required concentration just before use. The stock solutions and the samples were stored in dark bottles in refrigerator (6–8° C.). Disc diffusion assay (Bauer, A. W., et al, *American J. Clinical Pathology*, 1966, 45 (4): 493–496) was performed to detect the presence of antibacterial activities. The bacterial strains used in this study were obtained from Microbial Type Culture Collection (MTCC), Institute of Microbial Technology, Chandigarh; India. All bacteria were sub-cultured from −80° C. stock cultures into 5 ml of Mueller-Hinton broth and incubated for 24 h at desired temperatures. For use as an inoculum, the turbidity of the bacterial suspension was adjusted to the McFarland standard (0.5). Observations were recorded after 48 h of incubation of plates at desired temperatures. If the zone of growth inhibition recorded is high then, the antiseptic property of the disinfectant is also considered good. The data is recorded in table-2.

TABLE 2

Zone of growth inhibition produced by the surface disinfectant '"SW"' and hand disinfectant 'HK' against pathogenic bacterial strains.

| Bacterial strains* | EF | BS | MS | SE | SA | SM | EA | YE | SY | KP | PA | EC |
|---|---|---|---|---|---|---|---|---|---|---|---|---|
| (A)SW undiluted | 25 | 25 | 20 | 20 | 16 | 20 | 12 | 10 | 9 | 11 | 7 | 17 |
| 1/10 diluted | 18 | 18 | 16 | 16 | 14 | 16 | 10 | 5 | 6 | 9 | 1 | 14 |
| 1/100 diluted | 11 | 10 | 12 | 12 | 9 | 12 | — | — | — | — | — | 6 |
| (B)HK undiluted | 13 | 14 | 13 | 15 | 13 | 12 | 3 | 2 | 2 | 3 | 2 | 5 |
| 1/10 diluted | 2 | 6 | 4 | 7 | 7 | 2 | — | — | — | — | — | — |

*Abbreviations are as described in table-1

EXAMPLE-6

Evaluation of the Anti-Fungal Properties of the Disinfectants

Antifungal activity testing of the disinfectants was done as per (Wannisorn, et al, Antifungal activity of lemon grass oil and lemon grass oil cream. *Phytotherapy Research* 10, 551–554, 1996). Fungal cultures were grown on SDA at 28° C. for seven days. Suspension of each fungus was prepared in 0.85% normal saline containing 0.1% Tween 80. For use as inoculum, the turbidity of the fungal suspensions was also adjusted to the McFarland standard 0.5.

Two-fold serial dilution technique was employed to assess the minimum inhibitory dilution (MID) of a given compound. In each assay 20 μL of fungal culture (ca.0.7×10$^5$ spores or 0.2×10$^5$ CFU in the case of yeast) prepared as before was added to medium in a tube, which was, incubated under appropriate culture conditions and examined by visible turbidity. The MID was treated as the lowest dilution of the test compound, which inhibited the appearance of visible growth. The antifungal property of both the disinfectants is shown in table-3.

TABLE 3

The minimal inhibitory dilution factor of the surface disinfectant 'SW' and hand disinfectant 'HK' against pathogenic fungal strains.

| Fungal strains* | CA | CI | MG | SS | CN |
|---|---|---|---|---|---|
| SW (A) | 1/12800 | 1/12800 | 1/3200 | 1/6400 | 1/3200 |
| HK (B) | 1/160 | 1/160 | 1/6400 | 1/3200 | 1/320 |

*Abbreviations are as described in table-1

EXAMPLE-7

Practical Test on Volunteers

Hands and palms of 36 volunteers was soiled with the clay collected from the garbage site and thumb impression was made on the surface of the sterile nutrient agar plate @ 20 plates/volunteer before and after cleaning the thumb with cotton swab containing hand disinfectants at the recommended dose. Thumb impressions made after washing with water was taken as control. The exposed plates were then incubated for 3 days for 37° C. The amount of growth of microbes on the agar plates were observed and scored in terms of percentage. Presence of even a single colony i.e., the single cell was considered as not effective. Hence, a volunteer reporting no microbial growth in any of the 20 plates indicate 100% killing efficiency.

| | Percent killing of bacteria* Hand disinfectant treated | | |
|---|---|---|---|
| Volunteer | 100 | 90 | <90 |
| 1 | + | − | − |
| 2 | + | − | − |
| 3 | + | − | − |
| 4 | − | + | − |
| 5 | + | − | − |
| 6 | + | − | − |
| 7 | − | + | − |
| 8 | + | − | − |
| 9 | + | − | − |
| 10 | + | − | − |
| 11 | + | − | − |
| 12 | + | − | − |
| 13 | + | − | − |
| 14 | + | − | − |
| 15 | + | − | − |
| 16 | + | − | − |
| 17 | + | − | − |
| 18 | + | − | − |
| 19 | + | − | − |
| 20 | − | + | − |
| 21 | + | − | − |
| 22 | + | − | − |
| 23 | − | + | − |
| 24 | + | − | − |
| 25 | + | − | − |
| 26 | + | − | − |
| 27 | + | − | − |
| 28 | + | − | − |
| 29 | + | − | − |
| 30 | + | − | − |
| 31 | + | − | − |
| 32 | + | − | − |
| 33 | − | + | − |
| 34 | + | − | − |
| 35 | + | − | − |
| 36 | + | − | − |
| 37 | + | − | − |
| Totalpositive | 32 | 05 | 0 |

*No killing was observed after washing the hand with tap water.
+ Killing occurred
− No killing occurred From the data presented above it is clearly evident that nearly 32/37 i.e., 86% of the volunteers reported 100% killing efficiency after treatment with surface disinfectant. Another 14% reported 90% or above killing efficiency.

EXAMPLE-8

Method of Use of the Surface Disinfectant 'SW'

The surface disinfectant 'SW' is used to clean and effectively decontaminate any hard surface. If the surface to be used is heavily soiled and is expected to contain a heavy microbial load such as in hospitals and high-risk areas, then it is used undiluted to obtain the best results. In this case the disinfectant is applied onto a piece of soft wet cloth and the same is spread over the infected area and left for 5 minutes for effective disinfection. For medium risk areas the disinfectants are used after diluting ten folds in water. The dilution is done typically in a bucket of water and the spreading is done as before. The disinfectant is used after 100-fold dilution for low risk area such as house and offices.

EXAMPLE-9

Method of Use of the Hand Disinfectant 'HK'

The hand disinfectant 'HK' is used to clean and effectively decontaminate hand and other surfaces like laminar clean air-flow, operation table before surgery. Pour out a few drops of hand disinfectant 'HK' and rub well over hands for 30 sec. It is absolutely safe and non-toxic and can be used in the microbiology to cell culture laboratories and for practicing surgeons. It gives a healthy environment to all researchers and professionals and also a bio-safe hand wash for household and toiletries.

What is claimed is:

1. A homogeneous, clear and transparent composition for cleaning hands and other human skin surfaces, said composition comprising:

| | |
|---|---|
| a. Oil obtained from the plant *Mentha spicata* var. viridis: | 0.01–0.05% |
| b. Menthol menthyl acetate: | 0.05–0.5% |
| c. Ethanol: | 1–25% |
| d. Isopropanol: | 5–50% |
| e. Benzalkonium chloride: | 0.1–0.5%, and |
| f. Distilled water: | to make up the volume. |

2. A composition as claimed in claim 1 wherein the composition comprises:

| | |
|---|---|
| a. *Mentha spicata* var. viridis oil: | 0.02% |
| b. Menthol menthyl acetate: | 0.10% |
| c. Ethanol: | 5.00% |
| d. Isopropanol: | 30.00% |
| e. Benzalkonium Chloride: | 0.30%, and |
| f. Distilled water: | to make up the volume. |

3. A homogeneous, clear and transparent composition for cleaning surfaces such as floor, said composition comprising:

| | |
|---|---|
| a. *Mentha spicata* var. viridis oil: | 0.01–0.05% |
| b. Citronella oil: | 0.005–0.05% |
| c. 2-ethoxyethanol: | 0.05–1.0% |
| d. Benzalkonium chloride: | 0.05–5.0% |
| e. Sodium hydroxide: | 0.0001–0.2 N, and |
| f. Sodium lauryl sulphate: | 0.001–1.0% |

4. A composition as claimed in claim 3 comprises:

| | |
|---|---|
| a. *Mentha spicata* var. viridis oil: | 0.02%; |
| b. Citronella oil: | 0.01% |
| c. 2-ethoxyethanol: | 0.1% |
| d. Benzalkonium chloride: | 0.1% |
| e. Sodium hydroxide: | 0.0005 N, and |
| f. Sodium lauryl sulphate: | 0.0025% |

5. A process for the preparation of a hand and surface cleaning and disinfectant composition as claimed in claim 1 and being effective against pathogenic bacteria and fungi, said process comprising the steps of: (HK)

a. providing *Mentha spicata* var. viridis oil to the extent of 0.01 to 0.05%, b. adding a 0.05 to 0.5% combination of menthol and menthyl acetate to the oil of step (a) and mixing thoroughly, c. adding 5 to 25% ethanol to the mix of step (b) and mixing thoroughly, d. adding 5 to 50% isopropyl alcohol to the mix of step (c) and mixing the entire combination thoroughly, e. adding distilled water to the mix of step (d) and mixing the entire combination thoroughly, and f. adding 0.1 to 0.5% benzalkonium chloride to the mix of step (e) and mixing the entire combination thoroughly to obtain a disinfectant composition.

6. A process as claimed in claim 5 wherein oil of *Mentha spicata* var. viridis is obtained from the leaves of the plant by hydro-distillation using Clevenger apparatus.

7. A process as claimed in claim 5 wherein a combination of menthol and menthyl acetate is prepared by mixing menthol and menthyl acetate in the ratio 40:60(w/v).

8. A process as claimed in claim 6 wherein menthol is obtained crystallization at minus 60° C. of oil isolated from the plant *Mentha arvensis*.

9. A process as claimed in claim 6 wherein menthol is obtained by direct or azeotropic esterification of menthol with acetic acid.

10. A process for the preparation of a surface such as floor, cleaning and disinfectant composition as claimed in claim 3, said process comprising the steps of:

a. providing *Mentha spicata* var. viridis oil to the extent of 0.01 to 0.05%, b. adding 0.005 to 0.5% citronellol oil to the oil of step (a) and mixing both thoroughly, c. adding 0.05 to 1% of 2-ethoxyethanol to the mix of step (b) and mixing the ingredients thoroughly, d. adding 0.05 to 5% benzalkonium chloride to the mix of step (c) and mixing the entire combination thoroughly e. adding 0.0001 to 0.2N % sodium hydroxide to the mix of step (d) and mixing the entire combination thoroughly, f. adding 0.001 to 1% sodium lauryl sulphate to the mix of step (e) and mixing the entire combination thoroughly, and g. distilled water to the mix of step (f) and mixing the entire combination thoroughly to obtain a surface cleaning and disinfectant composition.

11. A process as claimed in claim 10 wherein oil of *Mentha spicata* var. viridis is obtained from the leaves of the plant by hydro-distillation using Clevenger apparatus.

12. A process as claimed in claim 10 wherein the citronella oil is obtained from the leaves of plant commonly called 'Citronella' or *Cymbopogon winterianus*.

13. A process as claimed in claim 10 wherein the oil from the plant *Cymbopogon winterianus* is obtained by hydro-distillation.

14. A process for the preparation of a surface such as floor, cleaning and disinfectant composition as claimed in claim 3, said process comprising the steps of:

a. providing *Mentha spicola var. viridis oil to the extent of 0.01 to 0.05%, b. adding 0.005 to 0.5% citronellol oil to the oil of step (a) and mixing both thoroughly, c. adding 0.05 to 1% of 2-ethoxyethanol to the mix of step (b) and mixing the ingredients thoroughly, d. adding 0.05 to 5% benzalkonium chloride to the mix of step (c) and mixing the entire combination thoroughly, e. adding 0.0001 to 0.2N % sodium hydroxide to the mix of step (d) and mixing the entire combination thoroughly, f. adding 0.001 to 1% sodium lauryl sulphate to the mix of step (e) and mixing the entire combination thoroughly, and g. distilled water to the mix of step (f) and mixing the entire combination thoroughly to obtain a surface cleaning and disinfectant composition;

wherein the method of use of the surface disinfectant composition of claim 3 is applied onto a piece of soft wet cloth and the same is spread over the infected area and left for 5 minutes for effective disinfection.

15. A process for the preparation of a surface such as floor, cleaning and disinfectant composition as claimed in claim 3, said process comprising the steps of:

a. providing *Mentha spicala* var. viridis oil to the extent of 0.01 to 0.05%, b. adding 0.005 to 0.5% citronellol oil to the oil of step (a) and mixing both thoroughly, c. adding 0.05 to 1% of 2-ethoxyethanol to the mix of step (b) and mixing the ingredients thoroughly, d. adding 0.05% to 5% benzalkonium chloride to the mix of step (c) and mixing the entire combination thoroughly e. adding 0.0001 to 0.2N % sodium hydroxide to the mix of step (d) and mixing the entire combination thoroughly, f. adding 0.001 to 1% sodium lauryl sulphate to the mix of step (e) and mixing the entire combination thoroughly, and g. distilled water to the mix of step (f) and mixing the entire combination thoroughly to obtain a surface cleaning and disinfectant composition;

wherein the composition according to claim 3 is used to effectively clean decontaminate the surfaces are kitchen platform, ceramic tiles, marbles, cabinets, tables, and likewise.

16. A process for the preparation of a surface such as floor, cleaning and disinfectant composition as claimed in claim 3, said process comprising the steps of:

a. providing *Mentha spicata* var. viridis oil to the extent of 0.01 to 0.05%, b. adding 0.005 to 0.5% citronellol oil to the oil of step (a) and mixing both thoroughly, c. adding to 0.05 to 1% of 2-ethoxyethanol to the mix of step (b) and mixing the ingredients thoroughly, d. adding 0.05 to 5% benzalkonium chloride to the mix of step (c) and mixing the entire combination thoroughly e. adding 0.0001 to 0.2N % sodium hydroxide to the mix of step (d) and mixing the entire combination thoroughly, f. adding 0.001 to 1% sodium lauryl sulphate to the mix of step (e) and mixing the entire combination thoroughly, and g. distilled water to the mix of step (f) and mixing the entire combination thoroughly to obtain a surface cleaning and disinfectant composition;

wherein the composition according to claim 3, is used in the range of 1X to 100X.

17. A process for the preparation of a hand and surface cleaning and disinfectant composition as claimed in claim 1 and being effective against pathogenic bacteria and fungi, said process comprising the steps of:(HK)

a. providing *Mentha spicata* var. viridis oil to the extent of 0.01 to 0.05%, b. adding a 0.05 to 0.5% combination of menthol and menthyl acetate to the oil of step (a) and mixing thoroughly, c. adding 5 to 25% ethanol to the mix of step (b) and mixing thoroughly, d. adding 5 to 50% isopropyl alcohol to the mix of step (c) and mixing the entire combination thoroughly, e. adding distilled water to the mix of step (d) and mixing the entire combination thoroughly, and f. adding 0.1 to 0.05% benzalkonium chloride to the mix of step (e) and mixing the entire combination thoroughly to obtain a disinfectant composition;

wherein the composition according to claim 1 is used by pouring out a few drops and rubbing well over the hands for 30 sec.

* * * * *